United States Patent [19]

Kligman

[11] Patent Number: 4,752,472
[45] Date of Patent: Jun. 21, 1988

[54] COSMETIC SKIN TREATMENT USEING CYANOACRYLATE POLYMER FILM

[75] Inventor: Albert M. Kligman, Philadelphia, Pa.

[73] Assignee: Exovir, Inc., Great Neck, N.Y.

[21] Appl. No.: 843,738

[22] Filed: Mar. 25, 1986

[51] Int. Cl.[4] .............................................. A61K 31/78
[52] U.S. Cl. ....................................... 424/81; 514/844
[58] Field of Search ....................... 424/69, 81, 28, 33; 514/844

[56] References Cited

U.S. PATENT DOCUMENTS 4,246,257 1/1981 Elliott .................................... 424/69
4,473,569 9/1984 O'Sullivan ............................ 424/81
4,560,555 12/1985 Snider ................................... 424/78

Primary Examiner—Joseph L. Schofer
Assistant Examiner—Peter F. Kulkosky

[57] ABSTRACT

A method for the cosmetic treatment of human skin, particularly facial skin, for the removal of materials from the surface and the sebaceous follicles is disclosed. The method comprises applying a layer of liquid polymerizable adhesive to the skin, then applying a pliable adhesive tape to cover the applied liquid adhesive and allowing the polymerization of said layer of polymerizable adhesive to take place and then removing the layer of polymerized adhesive from the skin by stripping the tape from the skin. In this treatment the materials on the surface of the skin and within the sebaceous follicles being attached to and removed with the layer of polymerized adhesive along with the tape. Alpha-cyanoacrylate is usefully employed as the polymerizable adhesive in this treatment.

20 Claims, No Drawings

COSMETIC SKIN TREATMENT USEING CYANOACRYLATE POLYMER FILM

BACKGROUND OF THE INVENTION

This invention relatesd to the cosmetic treatment of facial skin and the like for the removal of materials from the skin surface and from the sebaceous follicles.

A technique known as "follicular biopsy", an extension of the non-invasive "surface biopsy", has been developed to extract the contents of sebaceous follicles so that the retrieved material can be examined histologically at the light or electron microscopic level, see the publication "The Follicular Biopsy" by O. H. Mills and A. M. Kligman, Dermatologica, 167, 57 (1983). The disclosures of this publication are herein incorporated and made part of this disclosure.

The follicles of human facial skin secrete a horny material (follicular horn) throughout the life of the individual. This material does not normally build up in the pores but is extruded and is removed by facial cleansing. At about age 50, and particularly in the skin of females, the follicles tend to dilate and fill up with horny material, which traps small vellus hairs. This debris distends the follicular orifices, giving them the appearance of blackheads. The surface of the skin becomes coarse and uneven. The lay term for these horny-filled follicles is "clogged pores".

In addition to the horny material in the follicles, other retention products such as bacteria (*P. acnes*) fungi (*P. ovale*) and a mite (*Demodex folliculorum*) contribute to the follicular debris.

Certain cutaneous disorders, such as acne, keratosis pilaris, ichthyotic states and fungal infections involve abnormal and excessive kerantinization. As does the age-related build up of follicular horn, these conditions also impart a course and inflamed look to the skin.

In all of the above described conditions, removal of the horny material and other debris from the follicles returns the follicles to their normal, healthy state and imparts a clear, smooth look to the skin surface. However, no simple method has heretofore existed for the removal of deep follicular horn and debris.

It would thus be desirable to provide a simple method for the complete removal of follicular horn and associated debris from the skin follicles.

Since removal of follicular horn and debris from the skin returns the skin to a clear, smooth state, such removal would be of a substantial interest to the cosmetics industry.

It is an object of the present invention to provide a cosmetic treatment for the removal of follicular horn and debris from the skin.

SUMMARY OF THE INVENTION

The invention is directed to the cosmetic treatment of facial skin and the like for the removal of materials from the surface and the sebaceous follicles of human skin. The cosmetic treatment comprises applying a layer of liquid polymerizable adhesive to the skin, allowing polymerization of the polymerizable adhesive, and removing or stripping the resulting layer of polymerized adhesive from the skin. In this treatment, the materials on the surface of the skin and the sebaceous follicles in contact with the applied polymerizable adhesive become attached to and removed with the stripped layer of polymerized adhesive.

Specifically, the cosmetic treatment involves the removal of surface material from the skin and from the sebaceous follicles of the skin by applying a thin layer or coating of a liquid polymerizable cyanoacrylate adhesive to the skin to be treated, followed by contacting the cyanoacrylate layer with an adhesive tape to adhere the tape to the cyanoacrylate layer and thus removing the polymerized cyanoacrylate layer from the skin by lifting or peeling or stripping away the tape away from the skin taking with it the polymerized cyanoacrylate layer and attached skin surface and follicular materials.

DETAILED DESCRIPTION OF THE INVENTION

This cosmetic treatment for the removal of follicular horn and debris from the skin pores comprises applying a liquid polymerizable alpha-cyanoacrylate to the skin to coat the skin and to enter and invade the affected pores so as to remove the unwanted material from the skin along with the resulting polymerized adhesive. The method not only completely cleans the skin and the pores of the skin but also imparts a healthy, clear and smooth look to the skin.

The liquid polymerizable adhesives of this invention are preferably cyanoacrylate-based adhesives such as liquid alpha-cyanoacrylate. Other liquid adhesives which produce similar results may be employed. Presently preferred are the alpha-alkyl cyanoacrylates such as alpha-methyl cyanoacrylate. The cyanoacrylate adhesive is presently used in the commercially available form, e.g. Krazy Glue adhesive, although agents which influence or increase or decrease the polymerization time, increase invasion of the applied cyanoacrylate adhesive into the pores and follicles and fragrances and surfactants and the like may be added.

The liquid cyanoacrylate adhesive is brushed or coated or applied onto the skin, after the skin has been prepared by washing and drying, using any convenient applicator or technique. The liquid adhesive quickly invades the follicles where it surrounds and infiltrates the horn and other debris within the follicles.

Before the adhesive completely polymerizes on the skin (usually within about three minutes) a flexible, pliable patch or backing or strip of adhesive tape is applied, sufficient to cover the treated area and pressed thereto so as to establish firm contact of the tape with the applied cyanoacrylate coating.

The backing or tape usually carries its own adhesive layer, and may be composed of paper, plastic, cloth or any flexible, pliable material. Presently preferred materials are the hypoallergenic adhesive coated tapes, such as Blenderm TM manufactured by 3M Company and Dermacil TM, Dermilite TM and Dermiclear TM manufactured by Johnson & Johnson. After applying the backing or tape to the treated area, about three minute elapses before the cyanoacrylate layer or coating is fully polymerized. When polymerized, an edge of the backing or tape is grasped, such as with the fingers or with any suitable instrument, and the backing pulled away from the skin.

Contents of the follicles remain attached to the backing due to the infiltration of the now-polymerized cyanoacrylate layer. A little discomfort is sometimes experienced when the backing is removed and when such discomfort is experienced, as may be evidence by some reddening of the treated skin, a hyper-emollient cream is applied to soothe any skin irritation.

While a variety of hyper-emollient creams may be employed, a presently preferred composition is as follows:

| Hyper Emollient Cream (Face and Body) | |
| --- | --- |
| Ultimata (Penreco White Petrolatum) | 6.5% |
| Frost (Penreco White Petrolatum) | 5.0% |
| Amercol-Cab | 30.0% |
| Cetyl Alcohol (95.0%) | 2.5% |
| Cyclochem-GMS-165 | 6.0% |
| Polawax | 3.0% |
| Myristyl Myristate (Croda) | 2.5% |
| Procetyl AWS | 2.5% |
| Crodamol PMP | 2.5% |
| Methyl Paraben | 0.2% |
| Propyl Paraben | 0.1% |
| Water | 30.7% |

Presently preferred treatment regimens are once every two to four weeks, or less frequent, such as once every 2–4 months, although certain conditions may require more frequent treatment for optimum effect. Treatment regimens of once per week for six weeks have been followed with no adverse effects noted.

EXAMPLE 1

A female patient with follicular horn buildup presented for treatment. The skin was washed with warm water and mild soap, and patted dry. Alpha methyl cyanoacrylate at ambient temperature was brushed onto an affected area of facial skin, leaving a thin layer of the unpolymerized adhesive. Within one minute, and before polymerization of the applied cyanoacrylate layer was completed, Blenderm TM adhesive tape was applied to cover the cyanoacrylate layer and pressed thereto. After approximately three minutes, the edge of the tape was grasped and the tape was pulled sharply away from the skin surface. On visual observation, material could be seen attached to the tape forming a pattern that reproduced the pattern of pores of the patient's skin.

This technique was repeated until all affected areas were treated. Treatment overlapping into unaffected skin areas frequently occurred but was not detrimental to the patient.

Following this cosmetic treatment, a hyperemollient soothing cream was rubbed onto the treated skin by the patient when it was noted that the skin was slightly red immediately after treatment.

Although the patient has presented with coarse, uneven skin that appeared to be dotted with blackheads, within four hours after the treatment the skin was clear and smooth, and the post-treatment redness had disappeared. Treatments were continued once per week for six weeks and no ill effects were noted. The treated skin looked healthy, clean and relatively smooth.

Although it is preferred to apply the tape to the adhesive coated skin before the adhesive has substantially completely polymerized, other suitable techniques as to when to apply the tape may be employed. The tape may be applied to the adhesive coating after the adhesive coating has completely polymerized. Also additional one or more coatings of the cyanoacrylate adhesive may be applied to the first applied adhesive coating, either before or after the first applied adhesive coating has polymerized and the tap then applied, also before or after the last applied adhesive coated has polymerized or otherwise reacted to form a coherent film or coating on the skin. In the practice of this invention the tape is applied to the adhesive coating such that when the tape is removed it takes with it and strips away the cyanoacrylate adhesive coating the skin, together with the skin surface debris and the follicular debris now fixed to the cyanoacrylate adhesive coating on the tape.

What is claimed is:

1. A method for the cosmetic treatment of facial skin and the like for the removal of materials from the surface and the sebaceous follicles of human skin which comprises applying a coating or film of liquid polymerizable cyanoacrylate adhesive to said ski, allowing the polymerization of said coating of polymerizable adhesive, and removing the coating of polymerized adhesive from the skin when adhesive is fully polymerized, the materials from the surface of the skin and the sebaceous follicles being attached to and removed with the layer of polymerized adhesive.

2. A method of claim 1, wherein the materials include bacteria, fungi, mites, and follicular horn.

3. A method of claim 1 wherein said coating of polymerizable adhesive comprises alpha methyl cyanoacrylate.

4. A method of claim 1, wherein said coating of polymerizable adhesive is applied at a substantially uniform thickness on the skin by brushing.

5. A method of claim 1, wherein said coating of polymerized adhesive is removed by contacting the layer with a second adhesive on a pliable backing or tape and lifting or peeling away said backing or tape from the skin.

6. A method of claim 5, wherein the backing or tape is cloth.

7. A method of claim 5, wherein the backing or tape is paper.

8. A method of claim 5, wherein the backing or tape is plastic such as polyester.

9. A cosmetic method for the removal of surface material from the skin and from the sebaceous follicles of the skin which comprises applying a thin, substantially uniform coating or film of a liquid polymerizable cyanoacrylate adhesive to the skin, contacting the cyanoacrylate layer with an adhesive tape, said tape adhering to said cyanoacrylate coating, and removing the polymerized cyanoacrylate coating or film from the skin when substantially fully polymerized by lifting or peeling away said tape away from the skin.

10. A method of claim 9, wherein the materials include bacteria, fungi, mites and follicular horn.

11. A method of claim 9, wherein the cyanoacrylate is alpha methyl cyanoacrylate.

12. A method of claim 9, wherein the tape is a plastic tape.

13. A method of claim 9, wherein the tape is a cloth tape.

14. A method of claim 9, wherein the tape is a paper tape.

15. A method of claim 9, wherein said coating or film of polymerizable adhesive is applied in an amount sufficient to uniformly wet and coat the skin surface to be treated.

16. A method according to claim 9, wherein another coating of polymerizable adhesive is applied to the coating of cyanoacrylate adhesive before contact with said adhesive tape.

17. A method according to claim 16, wherein said other coating of polymerizable adhesive is applied before polymerization of the first applied coating of liquid polymerizable cyanoacrylate adhesive.

18. A method according to claim 16, wherein said other coating of polymerizable adhesive is applied after polymerization of the first applied coating of liquid polymerizable cyanoacrylate adhesive.

19. A method according to claim 16, wherein said adhesive tape is applied to said other coating of polymerizable adhesive before said other coating has polymerized.

20. A method according to claim 16, wherein said adhesive tape is applied to said other coating of polymerizable adhesive after said other coating has polymerized.

* * * * *